United States Patent
DeBruyn et al.

(10) Patent No.: US 8,092,559 B2
(45) Date of Patent: Jan. 10, 2012

(54) GENERATION OF HYDROGEN FROM HYDROCARBON BEARING MATERIALS

(75) Inventors: Roland P. DeBruyn, Highlands Ranch, CO (US); James B. Dodson, Castle Rock, CO (US); Robert S. Pfeiffer, Parker, CO (US); Eric L. Szaloczi, Denver, CO (US); Glenn A. Ulrich, Golden, CO (US); Jeffrey L. Weber, Denver, CO (US)

(73) Assignee: Luca Technologies, Inc., Golden, CO (US)

( * ) Notice: Subject to any disclaimer, the term of this patent is extended or adjusted under 35 U.S.C. 154(b) by 1024 days.

(21) Appl. No.: 11/568,974

(22) PCT Filed: May 6, 2005

(86) PCT No.: PCT/US2005/016124
§ 371 (c)(1),
(2), (4) Date: Jun. 22, 2007

(87) PCT Pub. No.: WO2005/113784
PCT Pub. Date: Dec. 1, 2005

(65) Prior Publication Data
US 2007/0248531 A1    Oct. 25, 2007

Related U.S. Application Data

(60) Provisional application No. 60/570,174, filed on May 12, 2004.

(51) Int. Cl.
*C12P 3/00* (2006.01)
*C01B 3/32* (2006.01)
*C12P 5/02* (2006.01)

(52) U.S. Cl. .................. 48/127.5; 435/168; 423/650
(58) Field of Classification Search ............... 48/127.5; 423/650; 435/168
See application file for complete search history.

(56) References Cited

U.S. PATENT DOCUMENTS

| | | |
|---|---|---|
| 1,990,523 A | 2/1935 | Buswell et al. |
| 2,413,278 A | 12/1946 | Zobell |
| 2,641,566 A | 6/1953 | Zobell |
| 2,659,659 A | 11/1953 | Schmidl |
| 2,660,550 A | 11/1953 | Updegraff et al. |
| 2,807,570 A | 9/1957 | Updegraff |
| 2,907,389 A | 10/1959 | Hitzman |
| 2,975,835 A | 3/1961 | Bond |
| 3,006,755 A | 10/1961 | Adams |
| 3,185,216 A | 5/1965 | Hitzman |
| 3,332,487 A | 7/1967 | Jones |
| 3,340,930 A | 9/1967 | Hitzman |
| 3,437,654 A | 4/1969 | Dix |
| 3,637,686 A | 1/1972 | Kokubo et al. |
| 3,640,846 A | 2/1972 | Johnson |
| 3,724,542 A | 4/1973 | Hamilton |
| 3,800,872 A | 4/1974 | Friedman |
| 3,826,308 A | 7/1974 | Compere-Whitney |
| 3,982,995 A | 9/1976 | Yen et al. |
| 4,184,547 A | 1/1980 | Klass et al. |
| 4,300,632 A | 11/1981 | Wilberger et al. |
| 4,316,961 A | 2/1982 | Klass et al. |
| 4,329,428 A | 5/1982 | Ghosh et al. |
| 4,349,633 A | 9/1982 | Worne et al. |
| 4,358,535 A | 11/1982 | Falkow et al. |
| 4,358,537 A | 11/1982 | Chynoweth |
| 4,386,159 A | 5/1983 | Kanai |
| RE31,347 E | 8/1983 | Reijonen et al. |
| 4,416,332 A | 11/1983 | Wiberger et al. |
| 4,424,064 A | 1/1984 | Klass et al. |
| 4,446,919 A | 5/1984 | Hitzman |
| 4,450,908 A | 5/1984 | Hitzman |
| 4,475,590 A | 10/1984 | Brown |
| 4,481,293 A | 11/1984 | Thomsen et al. |
| 4,522,261 A | 6/1985 | McInerney et al. |
| 4,562,156 A | 12/1985 | Isbister et al. |
| 4,579,562 A | 4/1986 | Tarman et al. |
| 4,610,302 A | 9/1986 | Clark |
| 4,640,767 A | 2/1987 | Zajic et al. |
| 4,666,605 A | 5/1987 | Minami et al. |
| 4,678,033 A | 7/1987 | Killough |
| 4,743,383 A | 5/1988 | Stewart et al. |
| 4,826,769 A * | 5/1989 | Menger .................. 435/167 |
| 4,845,034 A * | 7/1989 | Menger et al. ............ 435/167 |

(Continued)

FOREIGN PATENT DOCUMENTS
DE          4036787 B1      5/1992
(Continued)

OTHER PUBLICATIONS

S. Brauer et al. "*Methanogenesis in McLean Bog, an Acidic Peat Bog in Upstate New York: Stimulation by H2/CO2 in the Presence of Rifampicin, or by Low Concentrations of Acetate,*" (Geomicrobiology Journal, Oct.-Nov. 2004, vol. 21, No. 7, pp. 433-443(11)), http://www.ingentaconnect.com, printed Apr. 26, 2005, 2 pgs.

Razvan Dumitru et al. "*Targeting Methanopterin Biosynthesis to Inhibit Methanogenesis,*" Applied and Environmental Microbiology, vol. 69, No. 12, Dec. 2003, pp. 7236-7241.

Wen-Sheng Dong et al. "*Hydrogen Production from Methane Reforming Reactions over Ni/MgO Catalyst,*" Bull. Korean Chem. Soc. 2001, vol. 22, No. 12, Aug. 11, 2001, 1 pg.

Hydrogen production in oil field production fluids with inactive methanogens. Data to be considered for incorporation into Luca's hydrogen patent, unauthored text, Mar. 9, 2005, 2 pgs.

Harry Braun, "*The Bad News About Natural Gas,*" Hydrogen News, Mar. 15, 2003, 2 pgs.

(Continued)

*Primary Examiner* — Herbert J Lilling
(74) *Attorney, Agent, or Firm* — Kilpatrick Townsend & Stockton LLP (57) ABSTRACT

Disclosed are strategies for the economical microbial generation of hydrogen, useful as an alternative energy source, from hydrocarbon-rich deposits such as coal, oil and/or gas formations, oil shale, bitumen, tar sands, carbonaceous shale, peat deposits and sediments rich in organic matter through the management of the metabolism of microbial consortia.

11 Claims, 4 Drawing Sheets

U.S. PATENT DOCUMENTS

| | | | |
|---|---|---|---|
| 4,883,753 A | 11/1989 | Belaich et al. | |
| 4,905,761 A | 3/1990 | Bryant | |
| 4,906,575 A | 3/1990 | Silver et al. | |
| 4,914,024 A | 4/1990 | Strandberg et al. | |
| 4,947,932 A | 8/1990 | Silver et al. | |
| 4,969,130 A | 11/1990 | Wason et al. | |
| 4,971,151 A | 11/1990 | Sheehy | |
| 5,044,435 A | 9/1991 | Sperl et al. | |
| 5,076,927 A | 12/1991 | Hunter | |
| 5,081,023 A * | 1/1992 | Yaginuma et al. | 435/76 |
| 5,083,610 A | 1/1992 | Sheehy | |
| 5,083,611 A | 1/1992 | Clark et al. | |
| 5,087,558 A | 2/1992 | Webster, Jr. | |
| 5,100,553 A | 3/1992 | Nomura et al. | |
| 5,155,042 A | 10/1992 | Lupton et al. | |
| 5,163,510 A | 11/1992 | Sunde | |
| 5,250,427 A * | 10/1993 | Weaver et al. | 435/42 |
| 5,297,625 A | 3/1994 | Premuzic et al. | |
| 5,327,967 A | 7/1994 | Jenneman et al. | |
| 5,340,376 A | 8/1994 | Cunningham | |
| 5,341,875 A | 8/1994 | Jenneman et al. | |
| 5,350,684 A | 9/1994 | Nakatsugawa et al. | |
| 5,360,064 A | 11/1994 | Jenneman et al. | |
| 5,363,913 A | 11/1994 | Jenneman et al. | |
| 5,368,099 A | 11/1994 | Davey et al. | |
| 5,424,195 A | 6/1995 | Volkwein | |
| 5,490,634 A | 2/1996 | Jain et al. | |
| 5,492,828 A | 2/1996 | Premuzic et al. | |
| 5,500,123 A | 3/1996 | Srivastava | |
| 5,510,033 A | 4/1996 | Ensley et al. | |
| 5,516,971 A | 5/1996 | Hurley | |
| 5,538,530 A | 7/1996 | Heaton et al. | |
| 5,551,515 A | 9/1996 | Fodge et al. | |
| 5,560,737 A | 10/1996 | Schuring et al. | |
| 5,593,886 A | 1/1997 | Gaddy | |
| 5,593,888 A | 1/1997 | Glaze et al. | |
| 5,597,730 A | 1/1997 | Aust et al. | |
| 5,630,942 A | 5/1997 | Steiner | |
| 5,670,345 A | 9/1997 | Srivastava et al. | |
| 5,695,641 A | 12/1997 | Cosulich et al. | |
| 5,723,597 A | 3/1998 | Kohne | |
| 5,763,736 A | 6/1998 | Daume | |
| 5,766,929 A | 6/1998 | Orolin et al. | |
| 5,783,081 A | 7/1998 | Gaddy | |
| 5,821,111 A * | 10/1998 | Grady et al. | 435/252.5 |
| 5,854,032 A | 12/1998 | Srivastava et al. | |
| 5,858,766 A | 1/1999 | Premuzic et al. | |
| 5,885,825 A | 3/1999 | Lin et al. | |
| 5,919,696 A | 7/1999 | Ikeda et al. | |
| 5,928,864 A | 7/1999 | Kohne | |
| 5,955,261 A | 9/1999 | Kohne | |
| 5,955,262 A | 9/1999 | Kourilsky et al. | |
| 6,090,593 A | 7/2000 | Fleming et al. | |
| 6,143,534 A * | 11/2000 | Menger et al. | 435/167 |
| 6,202,051 B1 | 3/2001 | Woolston | |
| 6,210,955 B1 | 4/2001 | Hayes | |
| 6,265,205 B1 | 7/2001 | Hitchens et al. | |
| 6,348,639 B1 * | 2/2002 | Crawford et al. | 435/262.5 |
| 6,420,594 B1 | 7/2002 | Farone et al. | |
| 6,543,535 B2 | 4/2003 | Converse et al. | |
| 6,758,270 B1 | 7/2004 | Sunde et al. | |
| 6,795,922 B2 | 9/2004 | Johnson et al. | |
| 6,859,880 B2 | 2/2005 | Johnson et al. | |
| 7,696,132 B2 | 4/2010 | Pfeiffer et al. | |
| 2001/0045279 A1 | 11/2001 | Converse et al. | |
| 2003/0062270 A1 | 4/2003 | McAlister | |
| 2003/0205458 A1 | 11/2003 | Roychowdhury | |
| 2003/0216353 A1 | 11/2003 | Mosher et al. | |
| 2003/0232423 A1 | 12/2003 | Priester et al. | |
| 2004/0033557 A1 | 2/2004 | Scott et al. | |
| 2004/0035785 A1 | 2/2004 | Rebholz | |
| 2004/0228833 A1 | 11/2004 | Costantino et al. | |
| 2005/0053955 A1 | 3/2005 | Sowlay et al. | |
| 2005/0269261 A1 | 12/2005 | Sublette | |
| 2006/0223153 A1 | 10/2006 | Pfeiffer | |
| 2006/0223159 A1 | 10/2006 | Pfeiffer | |
| 2006/0223160 A1 | 10/2006 | Vanzin | |
| 2006/0237097 A1 | 10/2006 | Lau et al. | |
| 2006/0254765 A1 | 11/2006 | Pfeiffer et al. | |
| 2007/0295505 A1 | 12/2007 | Pfeiffer et al. | |
| 2008/0299635 A1 | 12/2008 | Pfeiffer et al. | |
| 2010/0190203 A1 | 7/2010 | Pfeiffer et al. | |
| 2010/0248321 A1 | 9/2010 | Steaffens et al. | |
| 2010/0248322 A1 | 9/2010 | Pfeiffer et al. | |

FOREIGN PATENT DOCUMENTS

| | | |
|---|---|---|
| DE | 4115435 B2 | 8/1992 |
| DE | 19520548 B3 | 12/1996 |
| JP | 09 121868 B4 | 5/1997 |
| WO | WO 79/00201 B5 | 4/1979 |
| WO | WO 89/10463 A1 | 11/1989 |
| WO | WO 92/13172 A1 | 8/1992 |
| WO | WO 01/68904 A1 | 9/2001 |
| WO | WO 02/06503 A | 1/2002 |
| WO | WO 02/34931 A2 | 5/2002 |
| WO | WO 2004/071195 A1 | 8/2004 |
| WO | WO 2005/115648 A1 | 12/2005 |
| WO | WO 2007/022122 A1 | 2/2007 |
| WO | WO 2007/118094 A2 | 10/2007 |

OTHER PUBLICATIONS

CAN Europe, "Climate technology sheet #9: Hydrogen production," pp. 1-10, Pub Nov. 2003.

Karl Lang, "Coalbed Methane Trends," PTTC State-of-the-Art Technology Summary, Excerpts in PTTC Network News, 2nd Quarter 2000, http://www.pttc.org/tech_sum/statev6no2.htm, printed Mar. 26, 2004, pp. 1-6.

J.E. Zajic et al. "Microbial Hydrogen Production From Replenishable Resources," Int. J. Hydrogen Engergy, vol. 4, pp. 385-402, Publication Date 1979.

Derek R. Lovley et al. "Use of Dissolved H2 Concentrations to Determine Distribution of Microbially Catalyzed Redox Reactions in Anoxic Groundwater," ES&T Research, Eviron. Sci. Technol., vol. 28, No. 7, 1994, pp. 1205-1210.

Aitken, Carolyn M. et al "Anaerobic hydrocarbon degradation in deep subsurface oil reserves" Nature, Sep. 16, 2004, pp. 291-294.

Anderson, Robert T., and Lovley, Derek R., "Hexadecane Decay by Methanogenesis", Nature, v. 404, p. 722, Apr. 13, 2000.

Anderson, Robert T., Rooney-Varga, Juliette N., et al., "Anaerobic Benzene Oxidation in the Fe(III) Reduction Zone of Petroleum-Contaminated Aquifers", Environmental Science & Technology, v. 32, pp. 1222-1229, 1998.

Artech Inc., Biological Gasification of Coals. Final Report, U.S. Department of Energy, Contract DE-AC21-87MC23285, pp. 40-63, 1990.

Basiliko, Nathan et al. "Influence of Ni, Co, Fe, and Na additions on methane production in Sphagnum dominated Northern American peatlands" Biogeochemistry, 2001, 52: 133-153.

Batelle and Duke Engineering and Services; Surfactant-Enhanced Aquifer Remediation (SEAR) Design Manual; NFESC Technical Report TR-2206-ENV, Apr. 2002, 110 pgs: entire document; Naval Facilities Engineering Command Washington, DC 20374-5065 USA.

Belyaev, S. S., et al. "Methanogenic Bacteria from the Bondyuzhskoe Oil Field: General Characterization and Analysis of Stable-Carbon Isotopic Fractionation" Applied and Environmental Microbiology, 1983, v. 45, No. 2, pp. 691-697.

Bernard, F. P., et al. "Indigenous Microorganisms in Connate Water of Many Oil Fields: A New Tool in Exploration and Production Techniques" SPE 24811, 1992, pp. 467-476.

Biville, F. et al., "In vivo positive effects of exogenous pyrophosphate on Escherichia coli cell growth and stationary phase survival", Res. Microbiol. 1996, 147, 597-608.

Boopathy, R., "Anaerobic degradation of No. 2 diesel fuel in the wetland sediments od Barataria-Terrebone estuary under various electron acceptor conditions," Bioresource Technology 2003, vol. 86, pp. 171-175.

Brockman, Fred "Regulation of Microbial Communities" at http://www.sysbio.org/sysbio/microbial/index.stm, 2005, 2 pages.

Brown, L.R., and Vadie, A.A., "Slowing Production Decline and Extending the Economic Life of an Oil Field: New MEOR Technology", SPE 59306; SPE/DOE Improved Oil Recovery Symposium, Tulsa, Oklahoma, Apr. 3-5, 2000.

Budwill, Karen "Microbial Methanogenesis and its Role in Enhancing Coalbed Methane Recovery" (Canadian Coals) CSEG Recorder (Nov. 2003) pp. 41-43.

Business Wire, "U.S. Microbics opens new profit centr to outside customers; Bug factory brews microbe colonies for third party applications," Apr. 26, 2005, p. 1, 4 pgs.

Cervantes, Francisco J. et al, "Competition between methanogenesis and quinone respiration for ecologically important substrates in anaerobic consortia" FEMS Microbiology Ecology 34, 2000, pp. 161-171.

Claypool, George E. et al. "The Origin and Distribution of Methane in Marine Sediments" Natural Gases in Marine Sediments, Ed. Isaac R. Kaplan, 1974, pp. 99-139.

Claypool, Geroge E. "Geochemical Characterization of Biogenic Gas and Coalbed Methane in Shallow Gas Fields: Eastern Denver Basin, Powder River Basin and Williston Basin" Luca Technologies, Inc. Internal Report, Jul. 8, 2001, 29 pages.

Clayton et al. "Oil-Generating Coals of the San Juan Basin, New Mexico and Colorado, U.S." Org. Geochem. 1991, pp. 735-742, vol. 17, No. 6.

Clayton, C. et al. "Source Volumetrics of Biogenic Gas Generation" Bacterial Gas, Ed. R. Vially, 1992, pp. 191-204, Paris.

Coates, John D., Anderson, Robert T., et al., "Anaerobic Hydrocarbon Degradation in Petroleum-Contaminated Harbor Sediments under Sulfate-Reducing and Artificially Imposed Conditions", Environ. Sci. Technol., vol. 30, No. 9, pp. 2784-2789, 1996.

Connan, J. et al. Anaerobic biodegradation of petroleum in reservoirs: a widespread phenomenon in nature: 18th International Meeting on Organic Geochemistry Sep. 22-26, 1997 Maastricht, The Netherlands (Abstr.), p. O2: 5-6.

Connan, J. et al. "Origin of Gases in Reservoirs" 1995 International Gas Research Conference, 1996, pp. 21-41.

Conrad, R. "Contribution of hydrogen to methane production and control of hydrogen concentrations in methanogenic soils and sediments" FEMS Microbiology Ecology, 28 (1999) pp. 193-202.

DeBruin, R.H. et al. "Coalbed Methane in Wyoming" Wyoming State Geological Survey (Laramie, WY), Information Pamphlet 7 (second revision), 2004, 24 pages.

Donaldson et al., "Conference Focuses on Microbial Enhancement of Oil Recovery," The Oil and Gas Journal, pp. 47-52, Dec. 20, 1982.

Donaldson, Eric C. et al. Microbial Enhanced Oil Recovery, Developments in Petroleum Science, 1989, v. 22, pp. 1-14, 121, 123, 149, Elsevier.

Elias, Paul, "Mining for single-celled gold; Biotechs looking for cash in on Mother Nature's creations" Jul. 4, 2004, San Antonio Express-News, p. 3L, 3 pgs.

EP Supplemental Search Report mailed Nov. 5, 2010; Application No. 08771271.7, 6 pages.

Faber, E. et al. "Distinction of Bacterial and Thermogenic Hydrocarbon Gases" Bacterial Gas, Ed. R. Vially, 1992, pp. 63-74, Paris.

Ferry et al. 1976. Anaerobic Degradation of Benzoate to Methane by Microbial Consortium. Arch. Microbiol. 107, pp. 33-40.

Ficker et al., "Molecular Characterization of a Toluene-Degrading Methanogenic Consortium," Applied and Enviromental Microbiology, Dec. 1999, vol. 65, pp. 5576-5585.

Flesner, R. et al. "Pilot-scale base hydrolysis processing of HMX-based plastic-bonded explosives", 4th International Symposium on Special Topics in Chemical Propulsion: Challenges in Propellants and 100 Years After Nobel, May 27-31, 1996, pp. 213-220.

Flesner, R. et al. "Pilot-scale base hydrolysis processing of HMX-based plastic-bonded explosives", Chemical Abstracts, vol. 130, No. 5, Feb. 1, 1998, Columbus, Ohio, U.S.; Abstract No. 54464a, pp. 835.

Gaasterland, Terry "Archaeal Genomics" Current Opinions in Microbiology (1999) 2:542-547.

Galagan, James, E. et al. "The Genome of *M. acetivorans* Reveals Extensive Metabolic and Physiological Diversity" Genome Research 12: 532-542 (2002).

Grbic-Galic, D., and Vogel, T. "Transformation of Toluene and Benzene by mixed methanogenic cultures" Applied and Environmental Microbiology, 1987, v. 53, pp. 254-260.

Groudeva, V. I. et al. "Enhanced Oil Recovery by Stimulating the Activity of the Indigenous Microflora of Oil Reservoirs": Biohydrometallurgical Technologies (Eds. Torma, A. E., Apel, M.L.; and Brierlay, C.L.): Minerals, Metals, & Mater. Soc. Biohydromet. Technol. Int. Symp, 1993 (Jackson Hole, Wy. 93.8.22-25) Proc., v. 2, pp. 349-356.

Gullapalli, Irene L. et al., "Laboratory Design and Field Implementation of Microbial Profile Modification Process", SPE Reservoir Evaluation & Engineering, v. 3, No. 1, pp. 42-49, Feb. 2000.

Halbouty, M.T. "East Texas Field—USA, East Texas Basin, Texas; in Stratigraphic Traps II" (compiled by N.H. Foster, and E.A. Beaumont) AAPG Treatise of Petroleum Geology, Atlas of Oil and Gas Fields, 1991, pp. 189-206.

Hales, B.A. et al. "Isolation and Identification of Methanogen-specific DNA from Blanket Bog Peat by PCR Amplification and Sequence Analysis", Applied and Environmental Microbiology, 1996, pp. 668-675.

Hattori, Satoshi et al.; "*Thermacetogenium phaeum* gen.nov.,sp.nov., a strictly anaerobic, thermophilic, syntrophic acetate-oxidizing bacterium", Internation. Journal of Systematic and Evolutionary Microbiology (2000), 50, 1601-1609, 9 pages, 2000.

Hermann, M. et al. "Anaerobic Microflora of Oil Reservoirs: Microbiological Characterization of Samples from Some Production Wells" Bacterial Gas (R. Vially Ed.) Editions Technip. Paris, 1992, pp. 223-233.

Hunkeler et al., "Petroleum Hydrocarbon Mineralization in Anaerobic Laboratory Aquifer Columns," Journal of Contaminant Hydrology 32, pp. 41-61, 1998.

Intera In. and Naval Facilities Engineering Service Center; *Surfactant-Enhanced Aquifer Remediation (SEAR) Implementation Manual*; NFESC Technical Report TR-2219-ENV, Apr. 2003, 54 pgs: entire document; Naval Facilities Engineering Command Washington, DC 20374-5065 USA.

Ivanov, M. V. et al. "Additional Oil Production During Field Trials in Russia: Microbial Enhancement of Oil Recovery—Recent Advances " (4th US DOE MEOR Int Conf (Upton, NY, 1992) Proc; Elsevier Develop Petrol Sci Ser No. 39), 1993, pp. 373-381.

Ivanov, M. V. et al. "Die mikrobiologische Bildung von Methan in einer abzubauenden Erdollagerstatte" Frieberger Forschungshefte Reihe C, v., 1982, vol. 389, pp. 189-199.

Johnson et al., 1991, "Preliminary Results of a Coalbed Methane Assessment of the Wind River Indian Reservation, Whoming" Coalbed Methane, pp. 273-284.

Johnson, Ronald C. et al. "A Preliminary Evaluation of Coalbed Methane Resources of the Wind River Indian Reservation, Wyoming" Coal-Bed Methane Potential of the Wind River Indian Reservation, Ed. Stephen Manydeeds, Dec. 1991, pp. 40-64, Bureau of Indian Affairs Division of Energy and Mineral Resources.

Kasting, James F. "When Methane Made Climate" Scientific American, Jul. 2004, pp. 80-85.

Kim, Ann G. "Experimental Studies on the Origin and Accumulation of Coalbed Gas" U.S. Dept. of the Interior Bureau of Mines, Report of Investigations 8317, 1978, 18 pages.

Kim, Ann G. et al. "Hydrocarbon Gases Produced in a Simulated Swamp Environment" U.S. Dept. of the Interior Bureau of Mines, Report of Investigations 7690, 1972, 13 pages.

Klein, A. et al. "Comparative Analysis of Genes Encoding Methyl Coenzyme M Reductase in Methanogenic Bacteria", Mol Gen Genet, 1988, 213:409-420.

Krumholtz, Lee R. et al. "Confined subsurface microbial communities in Cretaceous Rock" Nature (Mar. 6, 1997) pp. 64-66.

Kunzig, Robert "20,000 Microbes Under the Sea" Mar. 2004, pp. 32-41 , vol. 25, No. 3.

Law, Ben E. et al "Coalbed Gas Accumulations in the Paleocene Fort Union Formation, Powder River Basin, Wyoming" Coalbed Methane—1991; Rocky Mountain Association of Geologists, pp. 179-190.

Le Blanc, Leonard, Artificial Recharge, Offshore, p. 10, Feb. 2000.

L'Haridon, S., Reysenbach, A.L., et al., Hot Subterranean Biosphere in a Continental Oil Reservoir, Nature, v. 377, pp. 223-224, Sep. 21, 1995.

Li, M. et al. "Advances in Simulated Tests of Biogas" Oil & Gas Geology, 1996, v. vol. 17, No. 2, pp. 117-122, with abstract.

Lollar, B. Sherwood et al. "Evidence for bacterially generated hydrocarbon gas in Canadian Shield and Fennoscandian Shield rocks" Geochemicaet Cosmochimica Acta vol. 57, pp. 5073-5085 (1993).

Lomans, Bart P. et al. "Isolation and Characterization of *Mehanomethylovorans hollandica* gen. nov., sp. nov., Isolated from Freshwater Sediment, a Methyltrophic Methanogen Able to Grow on Dimethyl Sulfide and Methanethiol." Applied and Env. Microbiology, Aug. 1999, p. 3641-3650, vol. 65.

Lovely, Derek R. "Deep Subsurface Microbial Processes" Reviews of Geophysics, 33, Aug. 3, 1995, pp. 365-381.

Luo Hong-Wei et al: "Differential expression of methanogenesis genes of *Methanothermobacter thermoautotrophicus*(former *Methanobacterium thermoautotrophicum*) in pure culture and in cocultures with fatty acid-oxidizing syntrophs": Applied and Environmental Microbiology , vol. 68, No. 3, Mar. 2002, pp. 1173-1179, XPOO2551248 ISSN: 0099-2240.

Magot, Michel et al. "Microbiology of Petroleum Reservoirs" Antonie van Leeuwenhoek, 2000, 77: 103-116.

Mattavelli, L. et al. "Deep Isotopic Light Methane in Northern Italy" Bacterial Gas, Ed. R. Vially, 1992, pp. 121-132.

McDonald, I.R. et al. "Molecular Ecological Analysis of Methanogens and Methanotrophs in Blanket Bog Peat" Microbial Ecology (1999) 38:225-233.

Menking et al., "Rapd Cleanup of Bacterial DNA from Field Samples", Elsevier, Resources, Conservation and Recycling 27 (1999), 179-186.

Middledorp et al., "Enrichment and Properties of a 1,2,4-trichlorobenzene-Dechlorinating Methanogenic Microbial Consortium," Applied and Environmental Microbiology, Apr. 1997, vol. 63, pp. 1225-1229.

Nandi, R et al. "Microbial Production of Hydrogen: An Overview" Critical Reviews in Microbiology, 24 (1): 61-84 (1998).

Nazina, T. N. et al. "Occurrence and Geochemical Activity of Microorganisms in High-Temperature, Water-Flooded Oil Fields of Kazakhstan and Western Siberia" Geomicrobiology Journal, 1995, v. 13, pp. 181-192.

Nazina, T. N. et al. "Microbial Oil Transformation Processes Accompanied by Methane and Hydrogen-Sulfide Formation" Geomicrobiology Journal, 1985, vol. 4, No. 2, pp. 103-130.

Neue, Heinz-Ulrich "Methane Emission from Rice Fields", BioScience, 1993, pp. 466-473, vol. 43, No. 7, downloaded from http://www.ciesin.org/docs/004-032/004-032.html.

Ng, T. K., and Weimer, P. J., "Possible Nonanthropogenic Origin of Two Methanogenic Isolates from Oil-Producing Wells in the San Miguelito Field, Ventura County, California", Geomicrobiology Journal, 1989, v. 7, pp. 185-192.

O'Carroll, Christopher "The Pervasive Presence of Microbes" http://www/umassmag.com/Summer_2003/The_pervasive_presence_of_microbes_5_08.html, 2003, 3 pages.

Ooteghem et al., "Hydrogen Production by the Thermophilic Bacterium, Thermotogo Neapolitana," Proceedings of the 2001 DOE Hydrogen Program Review, 2001, pp. 1-12.

Orphan et al., "Culture-Dependant and Culture-Independent Characterization of Microbial Assemblages Associated with High-Temperature Petroleum Reservoirs," American Society for Microbiology, pp. 700-711, 2000.

Panow, A. et al. "Mechanisms of Biologically-Mediated Methane Evolution from Black Coal", Fuel Processing Technology v. 52, pp. 115-125, 1997.

PCT International Search Report and Written Opinion mailed May 5, 2010; International Application No. PCT/US2010/028691; 12 pages.

Pedersen, K. "Exploration of Deep Intraterrestrial Microbial Life: Current Perspectives" FEMS Microbiology Letters 185 (2000) pp. 9-16.

Potter et al. "Artificial Recharge," Offshore, Feb. 2000, pp. 10.

Puri et al. "Enhanced Coalbed Methane Recovery" Proceedings 1990 SPE Annual Technical Conference and Exhibition Reservoir Engineering, Sep. 23-26, 1990, New Orleans, Louisiana, SPE 20732, 1990, pp. 193-202.

Rahman et al., "Towards efficient Crude Oil Degradation by a mixed bacterial consortium," Bioresource Technology, 2002, vol. 85, pp. 257-261.

Ravot, G. et al., "*Fusibacter paucivorans* Gen. Nov., Sp. Nov., an Anaerobic, Thiosulfate-Reducing Bacterium From an Oil-Producing Well," International Journal of Systematic Bacteriology (1999) 49, 1141-1147.

Reeve, John N. "*Archaebacteria* Then . . . *Archaes* Now (Are There Really No Archaeal Pathogens?)" Journal of Bacteriology, vol. 181, No. 12, Jun. 1999 pp. 3613-3617.

Revesz, K. et al. "Methane production and consumption monitored by stable H and C isotope ratios at a crude oil spill site, Bemidji, Minnesota" Applied Geochemistry, 1995, vol. 10, pp. 505-515.

Rice, Dudley D. "Controls, habitat, and resource potential of ancient bacterial gas", Bacterial Gas, Ed. Vially, R., 1992, pp. 91-118, Paris.

Rice, Dudley D. et al. "Characterization of coal-derived hydrocarbons and source-rock potential of coal beds, San Juan Basin, New Mexico and Colorado, U.S.A." International Journal of Coal. Geology, 1989, pp. 597-626, vol. 13.

Rice, Dudley D. et al. "Composition and Origins of Coalbed Gas" Hydrocarbons from Coal: American Association of Petroleum Geologists Studies in Geology #38, Eds. Law, B.E., and Rice, D.D., 1993, pp. 159-184.

Rice, Dudley D. et al. "Generation, Accumulation, and Resource Potential of Biogenic Gas" The American Association of Petroleum Geologists Bulletin, vol. 65, No. 1, Jan. 1981.

Rice, Dudley D. et al. "Identification and Significance of Coal-Bed Gas, San Juan Basin, Northwestern New Mexico and Southwestern Colorado" Geology and Coal-Bed Methane Resources of the Northern San Juan Basin, Colorado and New Mexico, Ed. J. Fassett, Coal-Bed Methane, San Juan Basin, 1988, pp. 51-59, Rocky Mountain Association of Geologists.

Rice, Dudley D. et al. "Nonassociated Gas Potential of San Juan Basin Considerable" Oil & Gas Journal, Aug. 1990, pp. 60-61, vol. 88, No. 33.

Ridgley, J.L. et al. "Re-Evaluation of the Shallow Biogenic Gas Accumulation, Northern Great Plains, USA—Is the Similar Gas Accumulation in Southeastern Alberta and Southwestern Saskatchewan a Good Analog?" Summary of Investigations (1999) vol. 1 pp. 64-78.

Rightmire, C.T. et al. "Coalbed Methane Resource", 1984, Coalbed methane resources of the United States, AAPG Studies in Geology #17, Tulsa, p. 1-B.

Rooney-Varga, Juliette N. et al. "Microbial Communities Associated with Anaerobic Benzene Degradation in a Petroleum-Contaminated Aquifer", Applied and Environmental Microbiology, v. 65, No. 7, pp. 3056-3063, Jul. 1999.

Rozanova, E.P. et al. "Distribution of Sulfate-Reducing Bacteria Utilizing Lactate and Fatty Acids in Anaerobic Ecotopes of Flooded Petroleum Reservoirs" Institute of Microbiology, Academy of Sciences of the USSR, Moscow. Translated from Mikrobiologiya, vol. 60, No. 2, pp. 360-367, Mar.-Apr. 1991.

Rozanova, E.P. et al. "Microbiological Processes in a High-Temperature Oil Field", Microbiology, v. 70, No. 1, pp. 102-110, 2000.

Schoell, Martin "Genetic Characteristics of Natural Gases" The American Association of Petroleum Geologists Bulletin, Dec. 1983, p. 2225-2238, vol. 67, No. 12.

Schoell, Martin et al. "Natural Sites of Bio-Conversion of CO2 and Hydrocarbons in the Subsurface: San Juan Basin and Michigan Basin" 2001 AAPG Annual Convention, Jun. 3-6, 2001, p. A180, abstract only.

Scott, A.R., Intergas'95, "Limitations and Benefits of Microbiallly Enhanced Coalbed Methane"; May 15-19, 1995—The University of Alabama Tuscaloosa, 10 pages, 1995.

Scott, Andrew R. "Composition and Origin of Coalbed Gases from Selected Basins in the United States" Proceedings of the 1993 International Coalbed Methane Symposium, University of Alabama/Tuscaloosa, May 17-21, 1993; pp. 207-222.

Scott, Andrew R. "Improving Coal Gas Recovery with Microbially Enhanced Coalbed Methane" in Coalbed Methane: Scientific, Environmental and Economic Evaluation; Eds. M. Mastaletcz, M. Glikson, and S. Golding, 1999, pp. 89-110, Kluwer Academic Publishers, Netherlands.

Scott, Andrew R. "Review of Key Hydrogeological Factors Affecting Coalbed Methane Producibility and Resource Assessment" Oklahoma Coalbed-Methane Workshop, 1999, pp. 12-36.

Scott, Andrew R. et al. "A New Energy Resource: Microbially Enhanced Gas Generation" 2001 AAPG Annual Convention, Jun. 3-6, 2001, p. A182, abstract only.

Scott, Andrew R. et al. "Composition, distribution, and origin of Fruitland Formation and Pictured Cliffs Sandstone gases, San Juan basin, Colorado and New Mexico", in S.D. Schwochow, D.K. Murray, and M.F. Fahy, eds., Coalbed methane of western North America: Denver, Rocky Mountain Association of Geologists, 1991, p. 93-108.

Scott, Andrew R. et al. "Limitations and Benefits of Microbially Enhanced Coalbed Methane" International Unconventional Gas Symposium (INTERGAS), May 15-19, 1995; pp. 423-432.

Scott, Andrew R. et al. "Microbially Enhanced Coalbed Methane: Limitations and Possible Benefits" AAPG Convention, 1995, p. 86A, abstract only.

Scott, Andrew R. et al. "Relation between basin hydrology and Fruitland gas composition, San Juan Basin, Colorado and New Mexico" Methane From Coal Seams Technology, Nov. 1991, pp. 10-18, vol. 9, No. 1.

Scott, Andrew R. et al. "Thermogenic and Secondary Biogenic Gases, San Juan Basin, Colorado and New Mexico—Implications for Coalbed Gas Producibility" AAPG Bulletin, Aug. 1994, v. 78, No. 8, pp. 1186-1209.

Smith, John W. et al. "Microbial Origin of Australian Coalbed Methane" AAPG Bulletin, vol. 80, No. 6 (Jun. 1996), pp. 891-897.

Smith, John W. et al. "The Stable Isotope Geochemistry of Australian Coals" Org. Geochem. vol. 3, 1982, pp. 111-131.

Springer, E. et al. "Partial Gene Sequences for the A Subunit of Methyl-Coenzyme M Reductase (Mcrl) as a Phylogenetic Tool for the Family *Methanosarcinaceae*", International Journal of Systematic Bacteriology, 1995, pp. 554-559.

Takashima, M. et al. "Mineral Requirements for Methane Fermentation" Critical Reviews in Environmental Control, vol. 19, Issue 5 (1990) pp. 465-479.

Ulrich, Glenn A. et al., "Active Biogenesis", *Energy*, Spring 2005, XP008128250, pp. 21-26.

Um, Y., "Isolation and characterization of polycyclic aromatic hydrocarbon-degrading microorganisms under methanogenic conditions," Dissertation, Universtity of Maryland, 2004, pp. 1-99.

Velji, M.I. et al., "The Dispersion of Adhered Marine Bacteria by Pyrophsphate and Ultrasound Prior to Direct Counting", published in IFREMER, Actes de Colloques, 3, 1986, pp. 249-259.

Volkwein, J.C. et al. "Biological Production of Methane from Bituminous Coal", Fuel Processing Technology, v. 40, pp. 339-345, 1994.

Weiner, J. M., and Lovley, D. R. "Rapid Benzene Degradation in Methanogenic Sediments from a Petroleum-Contaminated Aquifer", Appl. Environ. Microbiology 1998, vol. 64, No. 5, pp. 1937-1939.

Wellsbury, Peter et al. "Deep Marine biosphere fuelled by increasing organic matter availability during burial and heating" Nature 388, 573-576 (Aug. 7, 1997).

Whitfield, John "Origins of life: Born in a watery commune" Nature, (Feb. 19, 2004) pp. 674-676, vol. 427.

Whiticar, Michael J. "Correlation of natural gases with their sources" In: Magoon L. and W. Dow (eds.) The Petroleum System From Source to Trap, AAPG Spec. Publ. Memoir 60, 1994, Ch. 16, 261-83.

Whiticar, Michael J. et al. "Biogenic methane formation in marine and freshwater environments: CO2 reduction vs. acetate fermentation—Isotope evidence" Geochimica et Cosmochimica Acta, 1986, pp. 693-709, vol. 50, No. 5.

Zengler et al., "Methane Formation From Long-Chain Alkanes by Anaerobic Microorganisms," Nature, vol. 401, pp. 266-269, Sep. 16, 1999.

Zobell, C.E., "Bacterial Release of Oil From Sedimentary Materials," The Oil & Gas Journal, pp. 62-65, Aug. 2, 1947.

Van Ginkel, S., et al., "Biohydrogen Production as a Function of PH and Substrate Concentration", Environmental Science and Technology, American Chemical Society, Easton, PA, USA, vol. 35, No. 24, Dec. 15, 2001, pp. 4726-4730.

EP Supplementary Search Report mailed Oct. 12, 2010; Application No. 05747464.5; 7 pages.

\* cited by examiner

GENERATION OF HYDROGEN FROM HYDROCARBON BEARING MATERIALS

BACKGROUND OF THE INVENTION

The field of the present invention is microbial production of hydrogen through the management of the anaerobic or nearly anaerobic metabolism of consortia of microorganisms, including archaea and bacteria, to produce hydrogen, either in-situ or ex-situ, from hydrocarbon substrates such as coal, carbonaceous shale, oil, tar sands, bitumen, peat, and the like.

Because of the clean burning nature of hydrogen and its energy density on a weight basis, it is highly valued as an energy source. Billions of dollars of research have been expended on the invention and refinement of hydrogen fuel cells which have none of the carbon emissions associated with the use of fossil fuels. The greatest single obstacle to the widespread use of hydrogen fuel cells for motor transport and electricity generation is the high cost of molecular hydrogen on a cost per Btu basis relative to gasoline, coal, and natural gas. The present invention can dramatically lower the cost of hydrogen by utilizing microbial consortia to generate that hydrogen from the vast resources of coal, carbonaceous shales, oil, tar sands, bitumen and peat available throughout the world.

Currently, hydrogen is generated primarily by reformulation of methane by exposure to high pressure, high temperature steam. Most of the hydrogen liberated in this reaction is used in combination with nitrogen to make fertilizer. However, the Btu value of the hydrogen produced is far less than the Btu value of the fuel needed to produce it, making this an expensive and endergonic reaction that frustrates the widespread use of hydrogen as a transportation or electrical generation fuel.

Unlike the substrates in the present invention, agricultural waste, compost, municipal wastes including sewage and waste waters have been utilized as starting materials for fermentations to yield hydrogen gas. For example, Clostridia have been identified as important microorganisms for the microbial production of hydrogen gas from agricultural wastes, other cellulosic materials and sewage (JP 07031998 (1995), Van Ginkel et al. (2000) Ann. Conf. & Expos. on Water Quality and Wastewater Treatment, Water Environment Federation, 3413-3429; Nazinia, Tenn. (1981) Mikrobiologiia 50:163-166). A wide variety of heterotrophic microorganisms are known to produce hydrogen gas from organic waste products. Photosynthetic microorganisms such as species of *Rhodobacter, Rhodopseudomonas* and *Rhodospirillum* have also been proposed as microorganisms useful in the microbial production of hydrogen. A potential disadvantage of using photosynthetic microorganisms for phototrophic generation of hydrogen relates to limitations imposed on the penetration of light into a reactor containing a relevant substrate or where the substrate is underground, such as in massive sub-bituminous coal deposits containing billions of tons of coal and billions of pounds of hydrogen.

Despite the advances that have been made towards producing hydrogen from agricultural and municipal wastes, the limited availability and inconsistent composition and quality of these materials as well as the cost of hydrogen production through this process have precluded their use to date as substrates for the microbial production of hydrogen at quantities that could create a significant alternative source of energy relative to traditional fossil fuels (i.e. crude oil, natural gas, and coal). Furthermore, even assuming a substantial increase in biomass devoted to $H_2$ production, maximum total $H_2$ generated from agricultural and municipal wastes can provide less than 5% of current U.S. energy demand.

Research on microbial hydrogen production has focused exclusively on the conversion of waste products that contain easily fermentable materials including polysaccharides (Wang et al. 2003). For example, a myriad of cellulose-containing wastes produced in the food processing industry, agriculture, and domestic sewage have been evaluated as substrates to support microbial hydrogen production. Cellulose and other polysaccharides are easily fermentable (to hydrogen, carbon dioxide, acetate, and other organic acids) by a number of well characterized microorganisms and metabolic pathways. However, arguments have been made that microbial hydrogen production using these substrates will require very high conversion rates and efficiencies that have not been attained by the tested microorganisms (see, e.g. Benemann (1996)).

Even though there have been substantial technological advances in fossil fuel production techniques, the majority of oil discovered in the world remains trapped in the subsurface. Trapped crude oil in oil reservoirs, coals that may be too deep to excavate or that contain levels of impurities too high to burn, and carbonaceous shales that provide only a small amount of natural gas relative to the total hydrogen and energy within them represent a large source of substrate for microbial conversion to hydrogen.

There are numerous oil fields within the United States and around the world that are at or near the point of abandonment due to the inability to continue to produce oil from them profitably. Under current technology and oil prices, those fields will be abandoned with billions of barrels of oil remaining in place since primary and secondary oil recovery techniques still normally leave behind half or more of the original oil in place in those reservoirs at the time they are abandoned. That remaining oil represents a significant quantity of substrate for the generation of hydrogen that would otherwise be lost.

Hydrocarbon-bearing formations have been noted to contain variable amounts of hydrogen gas. See, e.g., Khorunzhii et al. (1977) Ugol'Ukrainy 4:42-44; Kosenko et al. (1967) Geologichnii Zhurnal 27:83-87. Although there is apparent recognition of the presence of some hydrogen in coal formations, it is unusual to detect hydrogen in hydrocarbon deposits. The present inventors are not aware of reports that document the microbial production of hydrogen from these materials or of commercial operations in which hydrogen is produced by microbial metabolism in coal-bearing or other hydrocarbon-rich environments.

By managing the metabolism of microorganisms to generate hydrogen, large amounts of that clean fuel can be made available for use. The substrate for that hydrogen generation is available in vast quantities in the form of coal, carbonaceous shale, tar sands, bitumen, peat, and the remaining oil in underground reservoirs.

SUMMARY OF THE INVENTION

The term "hydrogen" is used herein to denote both molecular hydrogen ($H_2$) and atomic hydrogen (H).

The present inventors have discovered that at least a portion of the hydrogen detectable in hydrocarbon deposits (coal, bitumen, oil shale carbonaceous shale, tar sands, peat, oil and/or gas formations, sediments rich in organic matter and the like) is produced by microbial metabolism. Furthermore, the inventors have discovered that in certain hydrocarbon formations the hydrogen is a major precursor for biogenic methane production. The present inventors have demonstrated that biosynthetic hydrogen generation can be enhanced by interventions that stimulate microorganism growth and metabolism in hydrocarbon formations.

It is an object of the present invention to provide a method for producing hydrogen through the management of the metabolism of microorganisms acting on hydrocarbons in natural materials, such as coal, bitumen, oil shale, carbonaceous shale, tar sands, peat, oil and/or gas formations, sediments rich in organic matter, and the like. This invention can be utilized either to produce that hydrogen as a free, molecular hydrogen end-product through the inhibition of its use by hydrogen consumers, such as methanogenic microorganisms, in the hydrocarbon substrate and the recovery of that free molecular hydrogen, or to allow the free hydrogen to be consumed by methanogenic microorganisms and recover that hydrogen as part of the methane or acetate produced by microorganisms. Hydrogen production can occur in-situ or it can occur ex-situ, for example, in a bioreactor, after removal of the hydrocarbon-rich material from the geologic formation in which it is found. The microbial metabolism can be achieved by the microflora which occurs naturally within the formation or it can be the result of metabolic reactions of one or more microorganisms introduced into the hydrocarbon rich geologic formation or bioreactor in which the hydrogen is produced.

In hydrocarbon deposits studied to date, the inventors have determined that $H_2$ availability is rate-limiting for biogenic methane production within the deposit. Enhancement of microbial hydrogen production can therefore lead to enhanced methanogenesis in the deposit, where that is the desired product.

The present inventors have determined that the production of hydrogen from hydrocarbon rich substrates, preferably in anaerobic or nearly anaerobic conditions, can be enhanced by several fold over natural microbial hydrogen production through the management of the metabolism of microorganisms that exist within or can be introduced into that hydrocarbon substrate, whether in-situ or ex-situ. The management of the consortia of microorganisms is achieved through selective introduction of nutrients, by other amendments to the substrate and the fluids contained therein, or through the introduction of new or alteration of existing microorganisms into the microbial consortia which are capable of producing hydrogen.

DETAILED DESCRIPTION OF THE INVENTION

In a particular embodiment, the environmental parameters of the hydrocarbon-rich materials are modified so as to improve production of hydrogen, for example by decreasing salinity or by introducing a nutrient (metal ion(s), nitrogenous compound(s), phosphorus-containing compound(s), vitamin(s), complex nutrients, or the like) which is limiting in the formation environment or in the reactor containing the hydrocarbon-rich natural material. Environmental factors which can be manipulated in the formation include, without limitation, temperature, salinity, sulfate content, water content, pH, nitrogen source and amount, phosphorous source and amount, trace elements and vitamins. It can be beneficial to measure the content of one or more chemical components of the formation or of the water within the formation in an effort to identify specific nutrient limitations to allow formulation of supplements useful to improve the rate and/or extent of hydrogen formation. The hydrogen which is evolved as the result of microbial metabolism is captured using equipment known to the art, such as that used for the capture of natural gas or methane. Where the gaseous material produced in the hydrocarbon rich geologic formation in the in-situ application of the invention or in a bioreactor in the case of ex-situ application of the invention is a mixture of gases, for example, consisting of carbon dioxide, methane and hydrogen, readily available separation technology can be employed so that one or more gases of interest can be collected. In addition, or in the alternative, one or more inhibitors of hydrogen-consuming microbial processes, including methanogenesis, acetogenesis or sulfate reduction, can be introduced into the hydrocarbon rich geologic formation or the bioreactor in an amount such that free molecular hydrogen accumulation is enhanced because of the inability of hydrogen consuming microorganisms to utilize that hydrogen due to the inhibitors introduced to prevent their metabolic consumption of that hydrogen.

Inhibitors of methanogenesis include for example, without limitation, 2-bromethanesulfonate (BESA) and certain derivatives of p-aminobenzoic acid. Inhibitors of acetogenesis include, for example, without limitation, monensin and tetracycline. In addition, the environmental parameters in the formation (or bioreactor) can be manipulated so as to selectively inhibit methanogens and/or other hydrogen-consuming microorganisms. Sulfate reduction by microorganisms and the concomitant consumption of hydrogen in that reaction is inhibited by molybdate. The addition of inhibitors is not required in environments with conditions that do not favor the terminal hydrogen-consuming reactions.

As specifically exemplified, for Powder River Basin coal core samples, hydrogen production is optimized through the amendment of the sample with an aqueous solution including metal ions. Desirably, the concentration of each metal ion (copper, iron, nickel and cobalt) in the solution is from about 0.005 to 10 mg/liter. Alternatively, or in addition, the solution can comprise minerals, including ammonium phosphate and/or additional compounds, and it can further, or alternatively, comprise a complex nutrient such as yeast extract (YE) or inexpensive waste products containing similiar complex nutrients such as those from fermentation plants, distilleries, breweries or bakeries, among others.

The microbial composition of the formation can itself be modified. It can be advantageous to analyze the geologic formation or the hydrocarbon-rich material from which hydrogen is to be produced to determine the presence of one or more particular microorganisms. In at least some instances, the nutritional and/or environmental preferences of the microorganism(s) which directly or indirectly effect hydrogen production are known, and by comparing the physical characteristics of the formation or hydrocarbon rich material with the preferences of at least one microorganism effecting hydrogen production, one recognizes the amendments to the formation or bioreactor which increase the rate or final yield of hydrogen production.

The anaerobic decomposition of complex sources of organic matter, including hydrocarbons, is catalyzed by microbial consortia. In general, the initial stages of decomposition include microbial depolymerization reactions and/or the production of organic acids, alcohols, hydrogen, and carbon dioxide. The organic acids and alcohols are further metabolized by other microorganisms to acetic acid, hydrogen, and carbon dioxide. The produced hydrogen and acetic acid are the primary substrates for the terminal members of the "anaerobic food chain" including methanogenic archaea, sulfate-reducing bacteria, and microorganisms that use oxidized metals, including ferric iron, as electron acceptors. Therefore, the anaerobic decomposition of organic matter is dependent on the interaction between these "cross feeding" functional groups within the consortia.

The importance of this "cross feeding" and of anaerobic microbial consortia in general, is perhaps best demonstrated by the finding that the bioconversion of many organic acids is often catalyzed via syntrophic metabolism. For example, in some ecosystems, many of the organic acids are biodegraded by syntrophic microorganisms that are dependent on the terminal members of the food chain (including methanogens and methanotrophs) to maintain hydrogen and/or acetate at low concentrations. Removal of particular metabolic intermediates and products, including hydrogen, either by collection or by further metabolism, can therefore enhance the conversion to hydrogen of complex hydrocarbons such as coal, oil, carbonaceous shales, bitumen, tar sands, and peat. The interactions between various functional groups of the consortia, and between the anaerobic or nearly anaerobic microbial consortia with the local environmental conditions in the formation, have a strong impact on the predominant metabolic pathways and the gaseous end-products produced (i.e. hydrogen, methane and/or carbon dioxide). Similarly, modification of one or more environmental parameters of the formation can influence metabolic activity.

In addition, the microbial populations within the formation can also be manipulated; one or more particular organisms or a microbial consortium or microbial consortia can be introduced to increase the rate of metabolism of the hydrocarbons to molecular hydrogen within the formation. The introduced microorganism(s) can have a genetic content which occurs in nature, or the genetic content of the microorganism(s) can be modified in the laboratory; i.e., a naturally occurring plasmid, transposon or other nucleic acid molecule can be introduced to optimize an existing metabolic capability or empower the microorganism or microorganisms to carry out a metabolic reaction which it or they had not been capable of previously. Alternatively, the introduced nucleic acid molecule can be one which has been created in the laboratory to optimize an existing metabolic capability or to encode one or more proteins which allow the microorganism or microorganisms into which it is introduced to carry out a metabolic reaction which it or they could not carry out in nature. Alternatively, the plasmid, transposon or other nucleic acid molecule introduced into a microorganism of interest can be created by joining portions of genetic material in the laboratory which do not occur joined in nature. For example, without wishing to be bound by any particular theory, the present inventors believe that benzoate metabolism is a bottleneck in the breakdown of complex hydrocarbon molecules to among other things, molecular hydrogen, in at least some hydrocarbon-rich formations. The specific enzymatic reactions within the benzoate-degrading microorganisms that limit benzoate metabolism can be targeted for genetic alteration. The nucleic acid molecule of interest can be introduced by any of a variety of ways known to the art, including but not limited to transformation, transfection, conjugation or transduction. In addition, the genetic content of a microbe of interest can be altered by selecting or screening for a novel phenotypic trait of interest, as is well known to the art.

While photoevolution of hydrogen is not likely to be practical in the context of hydrogen production from hydrocarbon deposits, certain of the phototrophic bacteria can evolve hydrogen through the action of formate hydrogenlyase during anaerobic, dark fermentation of organic substrates such as pyruvate (e.g., *Rhodospirillum rubrum*, see Drews and Imhoff (1991) in Variations in Autotrophic Life, Academic Press, NY, pp. 51-97). *Rhodopseudomonas palustris, Rhodobacter capsulatus, Rhodopseudomonas molischianum* and *Chromatium minutissimum* are nonlimiting examples of microorganisms that produce hydrogen with suitable carbon sources, such as glucose and formate, in the dark. Other electron donors for the microbial production of hydrogen (in the dark) can include, without limitation, organic acids, alcohols, amino acids and carbohydrates, depending on the microorganism or combination of microorganisms. For a review, see Sasikala et al. (1993) Adv. Appl. Microbiol. 38:211-295.

Environmental parameters within a formation can be assessed by obtaining either a solid phase sample such as a core sample, drill cutting and/or a sample of water, or gaseous or liquid samples, from within the formation. Appropriate parameters to assess in core samples include the presence and population of hydrogen-producing microorganisms and their activity, sulfate reducing microorganisms and their activity, methanogens and methanogenic activity, acetogens and acetogenic activity, gases including hydrogen, carbon dioxide, methane, and carbon monoxide, acetate and other organic acids, salinity, cation content, concentrations of copper, cobalt, zinc, iron, nickel, nitrogenous compounds, and phosphorus-containing compounds, sulfate content, water content and the content and the nature and amounts of carbonaceous materials. For aqueous samples taken from the formation, it is useful to measure one or more parameters including pH, salinity, concentrations of sulfate, sulfide, and acetic acid, metal content, nitrogen content and phosphorous content, among others. Information from the assessments can be used to determine optional supplementation of water or nutrient-containing compositions which can be pumped into the formation to improve hydrogen generation.

Core samples, preferably taken and maintained under anaerobic conditions, can be used to estimate the intrinsic rate of hydrogen (or other product) generation with or without supplementation with any nutritional parameter or inhibitor of interest. Desirably, surface microorganisms are not introduced as contaminants in the sample prior to culture experiments in the laboratory. In such cases, the sample is kept in a sealed environment. Methodologies for gas sampling and analysis are well known to the art.

By implementation of the present invention, the economic lives of abandoned oil fields and biogenic natural gas projects can be extended indefinitely by means of utilizing the existing infrastructure such as drilled and cased wells in those fields to access and manipulate those reservoirs as described herein to stimulate hydrogen production from them and to produce that hydrogen for beneficial use. Generating hydrogen in such a manner not only produces a clean fuel for use in motor transport and electricity generation, but it also reduces the need to drill new wells in potentially environmentally sensitive areas to access more natural gas. By utilizing the existing infrastructure in existing fields, the present invention can potentially save billions of dollars in capital expenditures while simultaneously generating a valuable energy source and minimizing the number of wells to be drilled to access that energy source.

Microbial consortia, either metabolically active or dormant, are present in environments which are rich in hydrocarbons, including deposits of coal, bitumen, oil, tar sands, peat, oil shales, natural gas deposits, carbonaceous shales, and sediments rich in organic matter. As used herein, hydrocarbons means compounds comprising at least hydrogen and carbon. In the context of this application, the term "microorganisms" is intended to encompass the bacteria and the archaea. Microorganisms can survive in and/or multiply in a wide range of environments, characterized by vast variations in temperature, pressure, pH, oxygen concentration, substrate availability and salinity. It is noted that not all microorganism strains can tolerate the entire ranges of environmental parameters. Thus, the present methods improve the metabolism of the consortia in hydrocarbon-rich environments, for example, in coal deposits, by altering reactor conditions or the in-situ geologic formation environment so that the microbial production of hydrogen gas (or other metabolic product(s) of interest) is maximized.

Methanogenesis is a metabolic process that commonly occurs in anaerobic sediments containing decomposing organic matter. Methane is often present within hydrocarbon-rich formations as adsorbed (onto solids), free, and dissolved methane. Some of the methane is "old" methane produced by methanogenesis upon sediment deposition or thermochemically upon sediment buried to significant depths; in many formations some of the methane is "new", i.e. it is newly synthesized via recent or ongoing methanogenesis. The present inventors have confirmed by use of radiotracers that microorganisms in all the coal samples tested to date are metabolically active. Methanogenesis, supported by the availability of molecular hydrogen to methanogenic microorganisms that consume that molecular hydrogen, has been detected in all coal samples that are free of sulfate, the presence of which has been seen to coincide with a lack of methane. Field geochemical signatures, attest to the occurrence of methanogenesis and hydrogen turnover in situ. That is, carbon and hydrogen isotope patterns of methane, carbon dioxide, and formation water also indicate the occurrence of methanogenesis supported by the presence of molecular hydrogen that is consumed by methanogens and acetogens.

The current invention utilizes complex and more recalcitrant hydrocarbon substrates in shales, coals, oils, and other carbonaceous materials as substrates for microbial hydrogen production. Prior to the current invention, these materials had not been tested as substrates for microbial hydrogen production. In contrast to cellulosic materials, the biodegradation of hydrocarbons is likely dependent on anaerobic microbial consortia. Specific microorganisms, metabolic pathways, and interactions between members of the consortia are not fully characterized. Results presented herein indicate that coal can be biodegraded via microbial consortia indigenous to the coal, and at significant rates once nutritional limitations are overcome. As opposed to widely dispersed cellulosic wastes, vast quantities of hydrocarbon within localized deposits are available as substrates for anaerobic microbial hydrogen production. For example, large quantities of coal at mines or coal fired power plants could be sites for ex-situ biosynthesis of hydrogen. In-situ application can occur within natural gas production fields (including oil, coal bed methane, and shales) with existing wells and transport facilities that can be converted for hydrogen production and distribution. Clearly, lower hydrogen conversion rates and efficiencies are required where larger quantities of substrate and existing infrastructure are available.

Although it is possible to introduce exogenous microorganisms with metabolic capabilities of interest, it is preferred to stimulate metabolic activities of the indigenous microorganisms. Limitations on microbial generation of a gas of interest, especially hydrogen but also potentially methane, include, but are not limited to, formation temperature, the nature and distribution of microorganisms within the hydrocarbon-rich deposit or formation, nutrient availability within the deposit (including vitamins, nitrogen, phosphorus, trace metals such as nickel, cobalt, iron and copper), the pH, availability of competing acceptors of reducing power such as sulfate or ferrous iron, and a lack of anaerobic conditions, among others. It is believed that it is easier to provide nutritional supplements as aqueous solutions or aerosols or water to the indigenous microorganisms than to transport microorganisms through a geologic formation, and the use of solutions of interest is less costly than maintaining and growing microorganisms at or near the formation. Water content and movement are also important factors from the standpoint of supporting microbial life and nutrient transport, respectively. An important physical factor is the permeability and/or fractures (natural or manmade) within the geologic formation as this affects nutrient and gas transport within the formation environment and affects collection of a gaseous products of interest such as hydrogen, and also potentially methane. Movement of introduced materials through the formation can be improved by fracturing and/or horizontal drilling.

We have demonstrated, in laboratory scale experiments, hydrogen gas accumulation in anaerobic coal slurries to approximately an order of magnitude greater than concentrations typically observed in anaerobic organic-rich environments where the rate of microbial hydrogen production is generally balanced by hydrogen consumption. The production of hydrogen in the coal slurries was proven to be effected by an anaerobic microbial consortium or consortia indigenous to the coal. Hydrogen gas accumulated to the greatest extent when coal biodegradation was stimulated by overcoming nutrient limitations, coupled with inhibiting methanogenesis, which was the predominant terminal electron accepting reaction and one of the hydrogen-consuming reactions in the coal samples. These results are believed to demonstrate for the first time the generation of hydrogen gas from coal using indigenous microorganisms. Other similar hydrocarbon-rich materials can also serve as substrates for microbial hydrogen production.

Methods and equipment for collection of gases from a formation are well known to the art. See, e.g., WO 02/34931 for a discussion. Strategies are also well known for optimum well placement in a geologic formation. Similarly, methods and equipment for collection of gaseous products from a bioreactor are also well known in the art. See, for example, U.S. Pat. No. 6,340,581.

All references cited in the present application are incorporated by reference herein to the extent that there is no inconsistency with the present disclosure.

The following examples are provided for illustrative purposes, and are not intended to limit the scope of the invention as claimed herein. Any variations in the exemplified articles that occur to the skilled artisan are intended to fall within the scope of the present invention.

EXAMPLES

Example 1

Core Samples

Core samples were obtained from regions of interest within coal beds. To minimize opportunities for microbial and/or chemical contamination of coal samples, no drilling muds were used during sample collection. The centers of core samples were desirably used for laboratory studies to further minimize the potential for contamination. The core samples were stored and transported in sealed stainless steel canisters which had been purged with argon to maintain an anaerobic environment so that obligately anaerobic microorganisms were not lost. In most cases, the majority of adsorbed gases were removed from the core samples prior to analysis or culture experiments.

Core samples from the Tongue River area in the northwest portion of the Powder River Basin, Dietz coal seam, were utilized for these experiments. The core was collected in the field in a manner that prevented oxygen exposure by placing it into a steel canister that was purged with argon. Gas in the core used for the experiments described herein was extensively desorbed during long-term storage and previous use.

Coal samples were passed through a small jaw crusher twice resulting in pulverized coal (to yield a particle size similar to that of granulated sugar) that was measured into serum bottles (5 g per bottle); manipulations were carried out in an anaerobic environment. Anoxic formation water that was collected from wells in the Dietz coal seam was added to the coal samples. Sodium sulfide (to 0.5 mM) was added to the water samples to ensure strict anoxic conditions in the coal slurries during long-term incubation. The bottles containing the coal slurries were sealed with butyl rubber stoppers and purged with helium, resulting in a small overpressure (~3 psi). Radioactively labeled $^{14}C$-bicarbonate was added to the incubations to trace methanogenic activity from hydrogen ($4H_2 + ^{14}CO_2 \rightarrow ^{14}CH_4 + 2H_2O$) in an effort to confirm the microbial production of methane from hydrogen gas.

Example 2

Nutritional Supplements

Nutritional supplements for stimulating coal biodegradation and hydrogen production were added to the coal slurries from anoxic stock solutions. Most of the nutritional supplements tested are inorganic compounds needed in very low or trace concentrations. These include a nitrogen source as ammonia, a phosphorous source as phosphate, a mixture of ammonia and phosphate, a mineral solution that contains phosphate, ammonia, and potassium, and yeast extract which contains a complex mixture of inorganic nutrients and organic precursors for cell growth. The compositions of the Mineral, Vitamin, and Trace Metal Solutions used in the experiments are listed in Tables 1-3. The Mineral Solution is a 200× concentrate, the Vitamin Solution is a 500× concentrate, and the Trace Metal Solution is a 100× concentrate.

TABLE 1

| Mineral solution[a] | |
|---|---|
| Component | Amt (g)/liter |
| Sodium chloride | 80 |
| Ammonium chloride | 100 |
| Potassium chloride | 10 |
| Potassium phosphate | 10 |
| Magnesium Sulfate × 7H$_2$O | 20 |
| Calcium chloride × 2H$_2$O | 4 |

[a] A solution containing the major inorganic components required for microbial growth

TABLE 2

| Vitamin solution[a] | |
|---|---|
| Component | Amt (g)/liter |
| Pyridoxine-HCl | 10 |
| Thiamine-HCl | 5 |
| Riboflavine | 5 |
| Calcium pantothenate | 5 |
| Thioctic acid | 5 |
| p-Aminobenzoic acid | 5 |
| Nicotinic acid | 5 |
| Vitamin B$_{12}$ | 5 |
| MESA[b] | 5 |
| Biotin | 2 |
| Folic acid | 2 |

[a] A solution designed to meet water-soluble vitamin requirements of many microorganisms
[b] Mercaptoethanesulfonic acid

TABLE 3

| Trace metal solution[a] | |
|---|---|
| Component | Amt (g)/liter |
| Nitrilotriacetic acid | 2.0 |
| Adjust pH to 6 with KOH | |
| Manganese sulfide | 1.0 |
| Ferrous ammonium sulfate | 0.8 |
| Cobalt chloride | 0.2 |
| Zinc sulfate | 0.02 |
| Copper chloride | 0.02 |
| Nickel chloride | 0.02 |
| Sodium molybdate | 0.02 |
| Sodium selenate | 0.02 |
| Sodium tungstate | 0.02 |

[a] A solution designed to meet the trace metal requirements of many microorganisms.

Sterile samples were autoclaved (120° C. for 20 minutes) on three occasions. Bromoethanesulfonic acid (BESA), a methanogen inhibitor, was added to selected incubations. Coal slurries without nutritional supplements or inhibitors were also prepared. Hydrogen production in the amended slurries relative to sterile coal slurries was measured to identify the degree of stimulation.

After approximately 134 days of incubation, all of the coal slurries were sampled for the aqueous phase (0.5 of 10 ml) and for gas analysis including hydrogen, methane, carbon dioxide, radioactive methane, and radioactive carbon dioxide. Methane and carbon dioxide were determined using a Hewlett Packard 5890 gas chromatograph equipped with a thermal conductivity detector. Radiolabeled methane and carbon dioxide were determined using a gas proportional counter (Innus Systems, Tampa, Fla.). Results are reported herein as mL hydrogen gas produced per kg of coal calculated on a per year basis.

The total quantity of hydrogen that was produced and consumed in the Dietz coal slurries was estimated as the sum of hydrogen that was consumed during methanogenesis to make methane, used by acetogenic microorganisms to make acetate, and the hydrogen that accumulated in the headspace of the incubations. The stoichiometric relationships of the hydrogen consuming processes identified in the coal samples with respect to hydrogen are:

$$4H_2 + CO_2 \rightarrow CH_4 + 2H_2O$$

$$4H_2 + 2CO_2 \rightarrow CH_3COOH(acetate) + 2H_2O.$$

Figure 1:
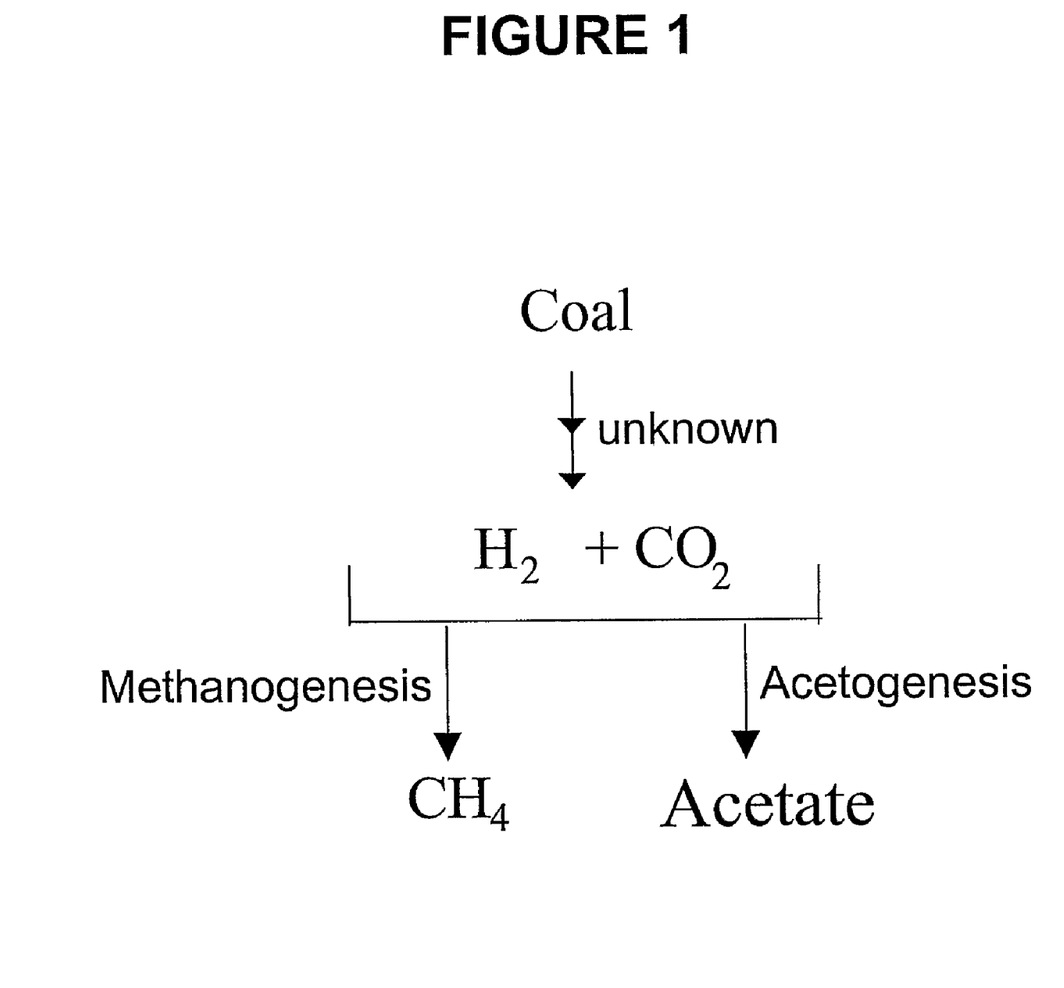
FIG. 1 shows a schematic diagram of the anaerobic microbial metabolic pathways detected in the tested coal seam.
Figure 2:
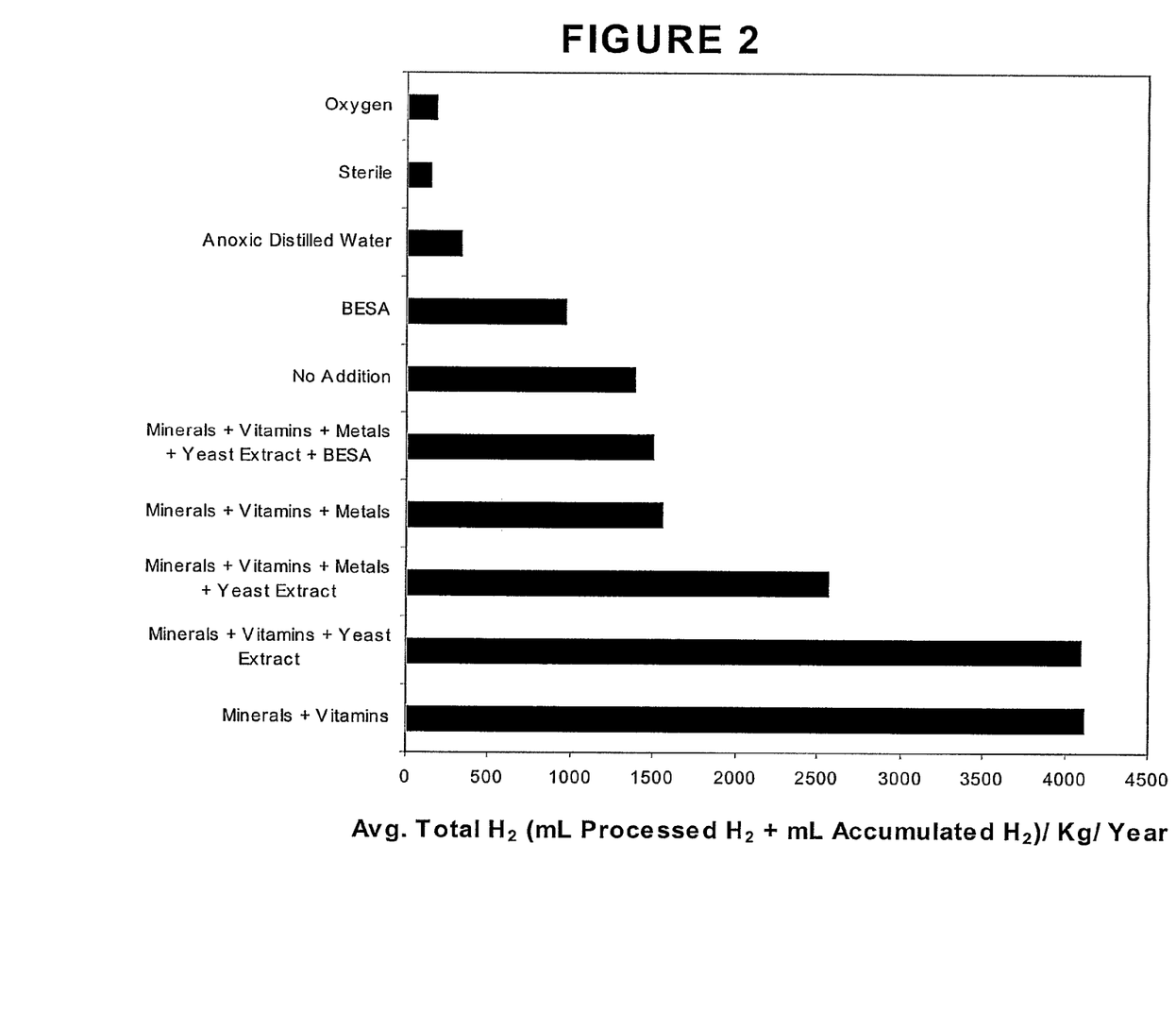
FIG. 2 is a bar graph showing total hydrogen processed, including hydrogen gas converted to methane and acetic acid as well as accumulated hydrogen gas, in sub bituminous coal (from the Dietz coal seam) slurries with various amendments as described.

Therefore, the calculation to estimate the total μmol of hydrogen that was processed (produced and consumed) is: (μmol $CH_4 \times 4$) + (μmol acetate × 4). This value was added to the quantity of hydrogen (in μmol) that accumulated in the headspace to obtain the total hydrogen values. FIG. 2 illustrates the average calculated total hydrogen processed with values shown (converted to units of mL $H_2$/kg/year) for triplicate Dietz coal slurries with a variety of treatments. All samples were analyzed together within 36 hours in order to minimize correction required for barometric pressure, instrumental variations and the like. Very little activity was observed in the sterile controls, thereby proving that the processed hydrogen is of biogenic origin. The highest total hydrogen value (about 4121 mL $H_2$/kg coal/yr; or about 0.6 lbs $H_2$/ton coal/yr) was obtained in incubations that were amended with a mixture of minerals and vitamins. Incubations amended with various nutrient supplements in combination with yeast extract also processed significantly higher quantities of hydrogen relative to the sterile and unamended (no nutrient supplements in addition to formation water) controls. Coal slurries that were treated with the methanogenic inhibitor BESA in combination with a minerals mixture, metals mixture, vitamins, and yeast extract, also processed significant quantities of hydrogen (primarily through acetate production, data not shown). This set of experiments confirms that significant quantities of hydrogen were processed in these coal slurries, especially when nutritional limitations of the microbial consortium or consortia were overcome.

Figure 3:
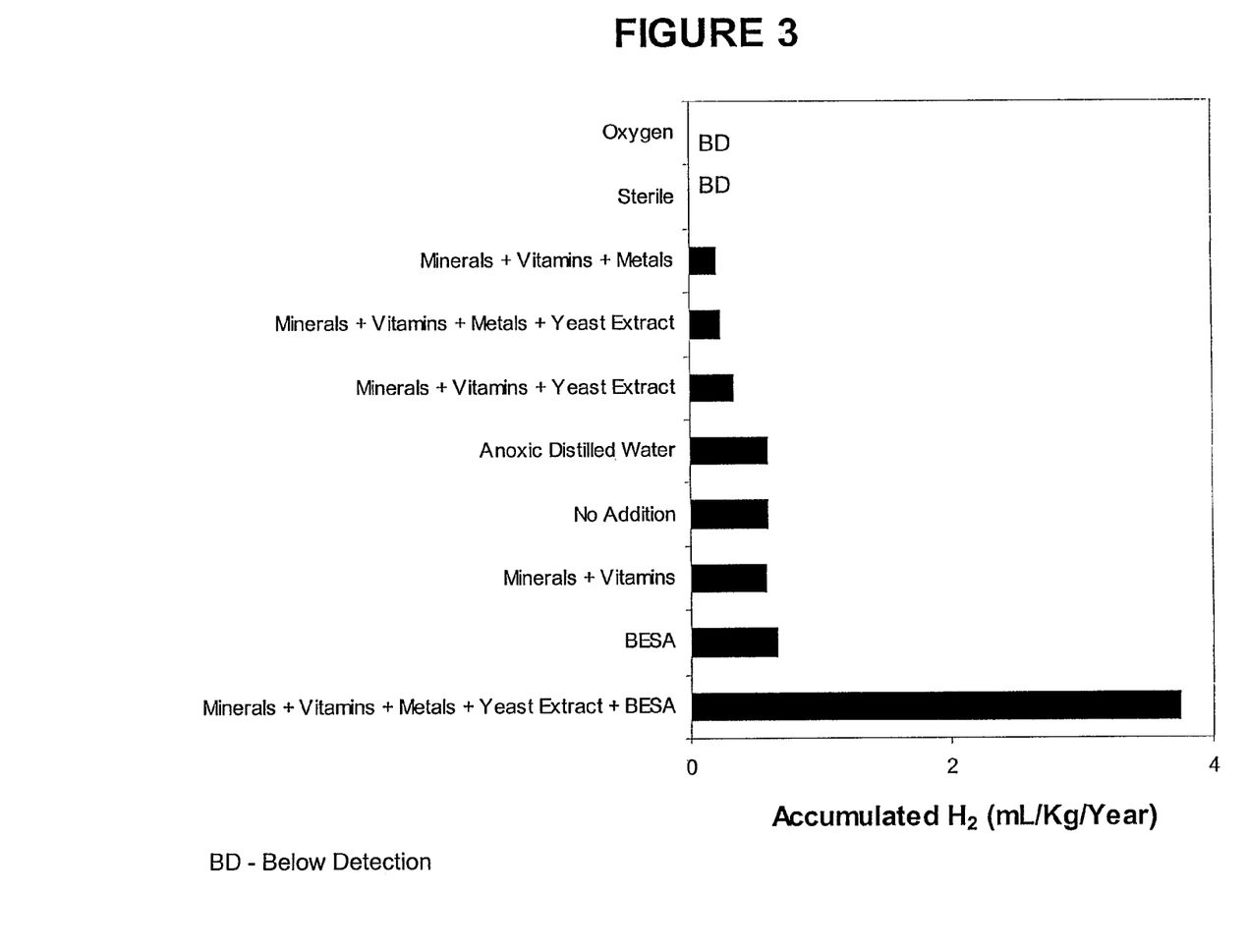
FIG. 3 shows the hydrogen gas accumulated during incubation of coal slurries (from the Dietz coal seam) with various amendments as described.

The quantity of hydrogen gas that accumulated in the headspace of the coal slurries is illustrated in FIG. 3. Hydrogen concentrations in the sterile slurries were below the detection limit (equivalent to approximately 0.003%). Hydrogen accumulated to the greatest extent when methanogenic activity was inhibited with BESA. For example, incubations supplemented with both BESA and a suite of nutrient supplements (minerals, metals, vitamins, and yeast extract) accumulated hydrogen to levels approximately an order of magnitude over the accumulation of a similarly stimulated sample (minerals and vitamins and metals and YE) without BESA. These experiments demonstrate the utility of inhibiting methanogenic activity, especially in concert with nutrient supplementation, to increase the production and accumulation of free, molecular hydrogen.

Figure 4:
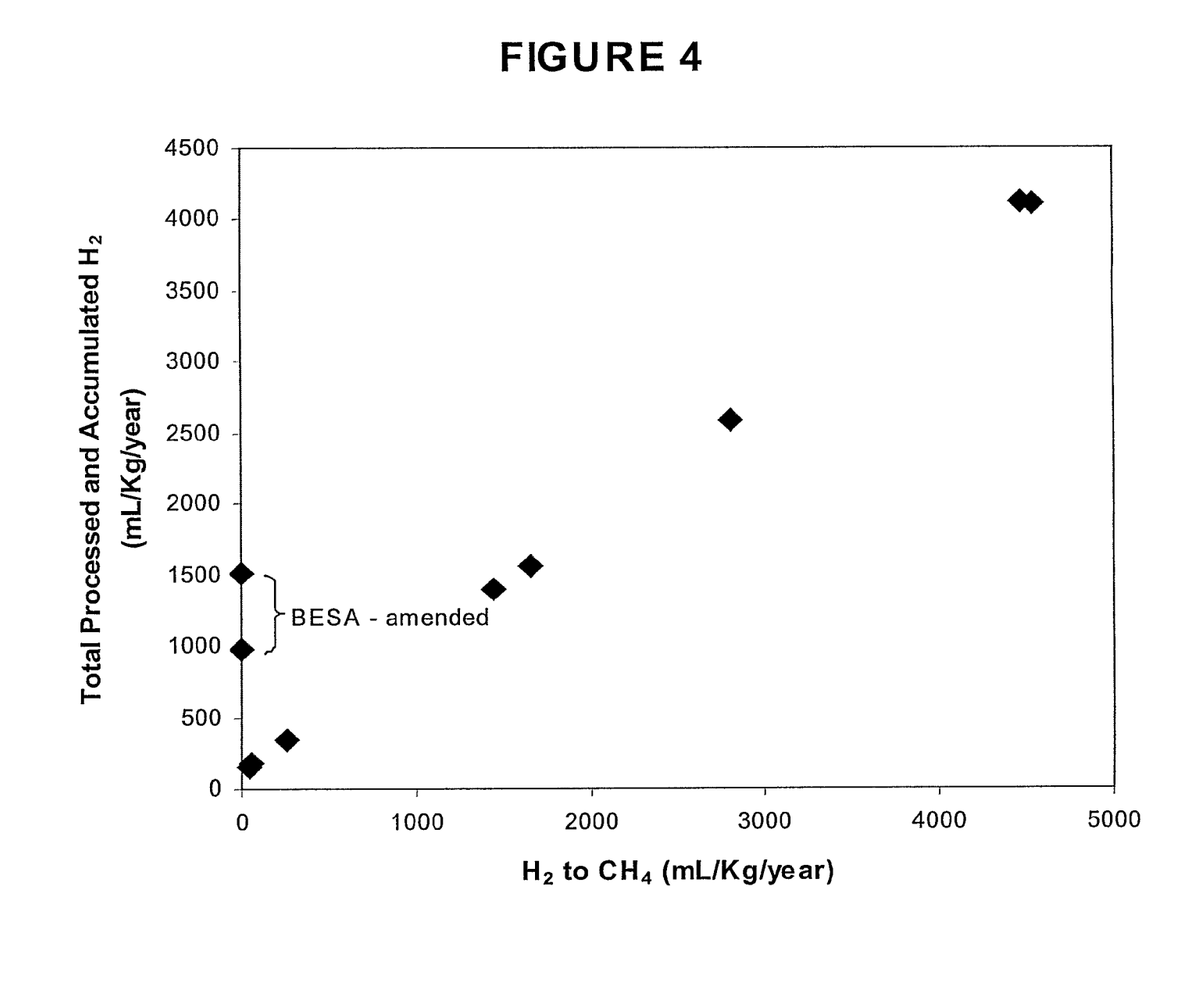
FIG. 4 is a graph showing increased methane production as a function of increased hydrogen production.

FIG. 4 graphically demonstrates the direct relationship observed between biogenic hydrogen production and methane synthesis. The data demonstrate that as hydrogen biosynthesis was increased, methane synthesis was increased in direct proportion. Even at the highest rate of hydrogen synthesis, the proportionality was observed, indicating that hydrogen biosynthesis was rate-limiting for methanogenesis in the samples that were studied. Two points on the ordinate demonstrate the effect of BESA as inhibitor of methane biosynthesis and resultant accumulation of hydrogen. It will be understood by those skilled in the art that in other types of hydrocarbon deposit, other formations biosynthetic hydrogen may be utilized in processes other than methanogenesis, for example in production of acetate. Since acetate is itself a product having economic value, stimulation of biogenic acetate production in such formations can be of value, in addition to the value of the hydrogen and/or methane produced.

In summary, these results indicate that the anaerobic bioconversion of the tested coals is, at least in part, restricted by the availability of nutrients within the formation water and coal samples used to prepare the slurries. When these nutrient limitations were alleviated, anaerobic coal bioconversion to produce hydrogen gas as an end product was stimulated or if methane is the targeted end product, the formation of molecular hydrogen as an intermediate can stimulate methane production. Hydrogen gas accumulation can be improved by inhibiting methanogenesis. Other hydrocarbon-rich substrates or formations including, but not limited to, oil and natural gas deposits, peat, bitumen, tar sands, carbonaceous shale and sediments rich in organic matter can be similarly treated to improve hydrogen production and/or accumulation.

What is claimed is:

1. A method for enhancing microbial production of methane from an in situ hydrocarbon-rich deposit, the method comprising:
   characterizing at least one environmental parameter for the in situ hydrocarbon-rich deposit located in a geologic formation;
   introducing an aqueous solution to the in situ hydrocarbon-rich deposit located in the geologic formation, wherein the aqueous solution stimulates a microbial consortium to increase a production rate for producing the methane from the in situ deposit; and
   collecting a gas mixture comprising the methane.

2. The method of claim 1, wherein the hydrocarbon-rich deposit is a deposit comprising oil, natural gas, coal, bitumen, tar sands, lignite, peat, carbonaceous shale or sediments rich in organic matter.

3. The method of claim 1, further comprising the step of characterizing at least one microorganism of the deposit.

4. The method of claim 1, wherein at least one microorganism of the deposit is genetically modified and reintroduced into the deposit so as to improve net production of acetate or methane by microorganisms in the deposit.

5. The method of claim 1, further comprising the step of introducing at least one microorganism into the hydrocarbon-rich deposit so as to improve net acetate or methane production.

6. The method of claim 1, wherein the at least one environmental parameter characterized comprises temperature, pH, salinity, sulfate concentration, acetate or other organic acid concentration, methane concentration, hydrogen concentration, water content, metal ion concentration and composition, or hydrocarbon concentration and/or composition.

7. The method of claim 1, wherein the aqueous solution comprises at least one component selected from the group consisting of complex nutrients, at least one vitamin, at least one metal ion, nitrogen, phosphorus, a trace element, an enzyme, a catalyst and a buffer.

8. The method of claim 7, wherein the at least one metal ion is copper, iron, cobalt, nickel or molybdenum.

9. The method of claim 1, wherein the aqueous solution is introduced into the deposit by injection into fractures and/or cleats within the deposit.

10. The method of claim 1, wherein the hydrocarbon-rich deposit is located in an anaerobic geologic formation.

11. A method for enhancing microbial production of a gas mixture comprising methane from an in situ hydrocarbon-rich deposit, the method comprising:
   introducing a catalyst to the in situ deposit, wherein the catalyst stimulates an increase in production of the methane from the in situ deposit by an amount in excess of the quantity of the catalyst introduced to the in situ deposit; and
   collecting the gas mixture comprising the methane.

* * * * *

(12) EX PARTE REEXAMINATION CERTIFICATE (9988th)
United States Patent
DeBruyn et al.

(10) Number: US 8,092,559 C1
(45) Certificate Issued: Dec. 17, 2013

(54) GENERATION OF HYDROGEN FROM HYDROCARBON BEARING MATERIALS

(75) Inventors: Roland P. DeBruyn, Highlands Ranch, CO (US); James B. Dodson, Castle Rock, CO (US); Robert S. Pfeiffer, Parker, CO (US); Eric L. Szaloczi, Denver, CO (US); Glenn A. Ulrich, Golden, CO (US); Jeffrey L. Weber, Denver, CO (US)

(73) Assignee: Transworld Technologies Limited, Houston, TX (US)

Reexamination Request:
No. 90/012,337, Jun. 5, 2012

Reexamination Certificate for:
Patent No.: 8,092,559
Issued: Jan. 10, 2012
Appl. No.: 11/568,974
Filed: Jun. 22, 2007

(21) Appl. No.: 90/012,337

(22) PCT Filed: May 6, 2005

(86) PCT No.: PCT/US2005/016124
§ 371 (c)(1),
(2), (4) Date: Jun. 22, 2007

(87) PCT Pub. No.: WO2005/113784
PCT Pub. Date: Dec. 1, 2005

Related U.S. Application Data (60) Provisional application No. 60/570,174, filed on May 12, 2004.

(51) Int. Cl.
*C01B 3/32* (2006.01)
*C12P 3/00* (2006.01)
*C12P 5/02* (2006.01)
*C01B 3/26* (2006.01)
*C09K 8/68* (2006.01)
*C10G 32/00* (2006.01)
*C10J 3/00* (2006.01)

(52) U.S. Cl.
CPC ... *C01B 3/32* (2013.01); *C01B 3/26* (2013.01); *C09K 8/68* (2013.01); *C10G 32/00* (2013.01); *C10J 3/00* (2013.01); *C12P 3/00* (2013.01); *C12P 5/023* (2013.01); *Y02E 50/343* (2013.01); *C10G 2300/1014* (2013.01); *C10G 2300/1025* (2013.01)
USPC .................. 48/127.5; 423/650; 435/168

(58) Field of Classification Search
None
See application file for complete search history.

(56) References Cited

To view the complete listing of prior art documents cited during the proceeding for Reexamination Control Number 90/012,337, please refer to the USPTO's public Patent Application Information Retrieval (PAIR) system under the Display References tab.

*Primary Examiner* — Timothy J Kugel (57) ABSTRACT

Disclosed are strategies for the economical microbial generation of hydrogen, useful as an alternative energy source, from hydrocarbon-rich deposits such as coal, oil and/or gas formations, oil shale, bitumen, tar sands, carbonaceous shale, peat deposits and sediments rich in organic matter through the management of the metabolism of microbial consortia.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-11 are cancelled.

\* \* \* \* \*